US010214465B2

(12) United States Patent
Frey et al.

(10) Patent No.: US 10,214,465 B2
(45) Date of Patent: Feb. 26, 2019

(54) PROCESSES FOR INCREASING THE OVERALL AROMATICS AND XYLENES YIELD IN AN AROMATICS COMPLEX

(71) Applicant: UOP LLC, Des Plaines, IL (US)

(72) Inventors: Stanley J. Frey, Palatine, IL (US); Patrick C. Whitchurch, Sleepy Hollow, IL (US); Keith A. Couch, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/994,945

(22) Filed: May 31, 2018

(65) Prior Publication Data

US 2018/0273444 A1 Sep. 27, 2018

Related U.S. Application Data

(63) Continuation of application No. PCT/US2016/065114, filed on Dec. 6, 2016.

(60) Provisional application No. 62/268,087, filed on Dec. 16, 2015.

(51) Int. Cl.

*C07C 5/367* (2006.01)
*C07C 5/27* (2006.01)
*C07C 6/12* (2006.01)
*C10G 69/06* (2006.01)
*C10G 69/12* (2006.01)

(52) U.S. Cl.

CPC .......... *C07C 5/2729* (2013.01); *C07C 5/2767* (2013.01); *C07C 5/367* (2013.01); *C07C 6/126* (2013.01); *C10G 69/06* (2013.01); *C10G 69/123* (2013.01)

(58) Field of Classification Search

CPC .. C07C 15/08; C07C 2/66; C07C 2/76; C07C 15/073; C07C 2/52; C07C 2/86; C07C 15/04; C07C 15/06; C07C 15/067; C07C 4/18; B01J 2229/42; B01J 29/44; B01J 2229/20; B01J 2229/36; B01J 29/7469; B01J 2229/26; B01J 29/005; B01J 29/12; B01J 29/22; B01J 29/67; B01J 29/74; B01J 29/7446; B01J 29/7453; B01J 29/7484; B01J 29/84; B01J 29/85; B01J 29/40; B01J 37/0009; B01J 37/20

See application file for complete search history.

(56) References Cited

U.S. PATENT DOCUMENTS

| | | | | |
|---|---|---|---|---|
| 4,062,903 | A | 12/1977 | Jacobson | |
| 7,553,998 | B2 * | 6/2009 | Bresler | C07C 5/2708 585/319 |
| 8,609,922 | B2 | 12/2013 | Werba et al. | |
| 2011/0245566 | A1 | 10/2011 | Bogdan et al. | |
| 2015/0094507 | A1 | 4/2015 | Gattupalli et al. | |
| 2015/0094512 | A1 | 4/2015 | Gattupalli et al. | |

FOREIGN PATENT DOCUMENTS

| | | | |
|---|---|---|---|
| CN | 103664489 | A | 3/2014 |
| WO | 2008094255 | A1 | 8/2008 |

OTHER PUBLICATIONS

Dupraz, Christian et al., "Integrating technologies for para-xylene production", Petrochemicals and Gas Processing, PTQ Autumn 1998, pp. 135-141.

Jeanneret, J.J. et al., "New strategies maximize para-xylene production", Process Technology, Hydrocarbon Processing, Jun. 1994, pp. 43-50.

Rault, Jacques et al., "Alternative routes to paraxylene production", Petrochemicals and Gas Processing, PTQ Spring 2004, pp. 123-129.

Rault, J. et al., "Maximizing Paraxylene Production with ParamaX", DGMK-Conference "The Future Role of Aromatics in Refining and Petrochemistry", Erlangen 1999, DGMK-Tagungsbericht 9903, ISBN 3-931850-59-5, pp. 131-138.

Product Profile: Paraxylene, updated from product profile, ECN 11, Jun. 2001, European Chemical News, Mar. 24-30, 2003, p. 14.

Search Report dated Mar. 16, 2017 for corresponding PCT Appl. No. PCT/US2016/065114.

* cited by examiner

*Primary Examiner* — Sharon Pregler

(57) ABSTRACT

The present subject matter describes processes for increasing overall aromatics and xylenes yield in an aromatics complex. More specifically, the process for increasing overall aromatics and xylenes yield in an aromatics complex accomplishes the increased yields by incorporating an $A_8$-$A_{10}$ isomerization step into the aromatics complex. This isomerization integration increases the para-xylene.

16 Claims, 2 Drawing Sheets

PROCESSES FOR INCREASING THE OVERALL AROMATICS AND XYLENES YIELD IN AN AROMATICS COMPLEX

CROSS-REFERENCE TO RELATED APPLICATIONS

This application is a Continuation of copending International Application No. PCT/US2016/065114 filed Dec. 6, 2016, which application claims priority from U.S. Provisional Application No. 62/268,087 filed Dec. 16, 2015, now expired, the contents of which cited applications are hereby incorporated by reference in their entirety.

FIELD

The present invention generally relates to aromatics production, and more particularly relates to processes for increasing the overall aromatics and xylenes yield in an aromatics complex.

BACKGROUND

An aromatics complex is a combination of process units that are used to convert naphtha, from a variety of sources, and pyrolysis gasoline into the basic petrochemical intermediates, benzene, toluene, and mixed xylenes. In aromatics applications, the naphtha is generally restricted to $C_6$+ compounds to maximize the production of benzene, toluene, and xylenes. The majority of the mixed xylenes are processed further within the aromatics complex, in a xylenes recovery section, to produce one or more individual aromatic isomers. As used herein, "mixed xylenes" contain four different $C_8$ aromatic isomers, including para-xylene which is used for the production of polyester fibers, resins and films.

Additional mixed xylenes may be produced from toluene, which is of low value, and heavy aromatics ($C_9$+ aromatics) (also referred to hereinafter as "heavies") that are present in reformate from the naphtha feedstock. Reformate is produced by selectively reforming the naphtha feedstock, in the presence of a reforming catalyst, to aromatics and high purity hydrogen. The naphtha feedstock is first hydrotreated to remove sulfur and nitrogen compounds and then sent to a reforming unit. In the reforming unit, paraffins and naphthenes in the naphtha feedstock are converted to aromatics, with as little aromatic ring opening or cracking as possible, producing "catalytically reformed naphtha".

To produce additional mixed xylenes from the low-value toluene and heavy aromatics ($C_9$+ aromatics), the aromatics complex may include a transalkylation process unit that is integrated between an aromatics fractionation section and the xylenes recovery section of the aromatics complex. The two major reactions in the transalkylation process unit are disproportionation and transalkylation. The conversion of toluene into benzene and mixed xylenes is called toluene disproportionation. Transalkylation is the conversion of a mixture of toluene, $C_9$ aromatics ($A_{9s}$), and $C_{10}$ aromatics ($A_{10s}$) into benzene and mixed xylenes. The process reactions are conducted in a hydrogen atmosphere to minimize coke formation on a transalkylation catalyst. As there is negligible aromatic ring destruction during the process, there is very little hydrogen consumption as a result of these reactions.

The catalytically reformed naphtha and pyrolysis gasoline feedstocks contain a large amount of phenyl groups substituted with ethyl, propyl, and butyl groups (collectively referred to herein as "higher alkyl groups"). Unfortunately, alkyl groups larger than methyl are cracked off of the phenyl group during transalkylation. "Dealkylation" refers to the complete or partial removal of the alkyl group(s). The scission of these higher alkyl groups leads to higher fuel gas yield, and higher benzene rather than more valuable para-xylene yield relative to the equivalent carbon number aromatic that had greater methyl group substitution. In addition, most of the hydrogen that is consumed during disproportionation and transalkylation is attributable to the cracking of non-aromatic impurities in the feedstock and such dealkylation of the ethyl, propyl, and butyl groups from the $C_9$ and $C_{10}$ aromatics.

Accordingly, it is desirable to provide processes for increasing overall aromatics and xylenes yield in an aromatics complex. It is also desirable to provide processes that increase the overall aromatics and xylenes yield in an aromatics complex that also reduce the amount of mass lost to fuel gas, and that shift the chemical equilibrium from benzene production to xylenes production while consuming less hydrogen. It is additionally desirable to provide processes for increasing overall aromatics and xylenes yield, while increasing conversion of toluene into mixed xylenes. Furthermore, other desirable features and characteristics of the present invention will become apparent from the subsequent detailed description of the invention and the appended claims, taken in conjunction with the accompanying drawings and this background of the invention.

SUMMARY

Processes are provided for increasing overall aromatics and xylenes yield in an aromatics complex. A process embodiment of the invention comprises a process for increasing overall xylenes yield in an aromatics complex, the process comprising the steps of separating an aromatics-rich reformate into a first hydrocarbon stream comprising $C_7$− hydrocarbons, a second hydrocarbon stream comprising $C_8$-$C_{10}$ aromatics, and a third hydrocarbon stream comprising $C_{10}$+ aromatics; isomerizing the second hydrocarbon stream comprising $C_8$-$C_{10}$ aromatics to produce a $C_8$-$C_{10}$ isomerization product stream; passing the $C_8$-$C_{10}$ isomerization product stream to a naphthene dehydrogenation zone to produce a naphthene dehydrogenation zone product stream; separating the naphthene dehydrogenation zone product stream into a first naphthene dehydrogenation zone product stream comprising $C_7$− hydrocarbons and a second naphthene dehydrogenation zone product stream comprising $C_8$+ aromatics; and passing the second naphthene dehydrogenation zone product stream comprising $C_8$+ aromatics to a xylenes recovery section.

An additional process embodiment of the invention comprises a process for increasing overall xylenes yield in an aromatics complex, the process comprising the steps of separating an aromatics-rich reformate stream into a first hydrocarbon stream comprising $C_7$− hydrocarbons, a second hydrocarbon stream comprising $C_8$-$C_{10}$ aromatics, and a third hydrocarbon stream comprising $C_{10}$+ aromatics; isomerizing the second hydrocarbon stream comprising $C_8$-$C_{10}$ aromatics in a isomerization zone to produce a $C_8$-$C_{10}$ isomerization product stream; separating the $C_8$-$C_{10}$ isomerization product stream into a first isomerization product stream comprising $C_7$− hydrocarbons and a second isomerization product stream comprising $C_8$+ aromatics fraction; passing the second isomerization product stream comprising $C_8$+ aromatics to an aromatics extraction zone to produce a first aromatics extraction zone product stream comprising $C_8$+ non-aromatics and a second aromatics extraction zone product stream comprising $C_8$+ aromatics; passing the first aromatics extraction zone product stream comprising $C_8$+ non-aromatics back to the isomerization zone; and passing the second aromatics extraction zone product stream comprising $C_8$+ aromatics fraction to a xylenes recovery section or transalkylation unit.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

Definitions

As used herein, the term “stream”, “feed”, “product”, “part” or “portion” can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated $C_1$, $C_2$, $C_3$, $C_n$ where “n” represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where “n” represents the number of carbon atoms in the one or more aromatic molecules. Furthermore, a superscript “+” or “−” may be used with an abbreviated one or more hydrocarbons notation, e.g., $C_3$+ or $C_3$−, which is inclusive of the abbreviated one or more hydrocarbons. As an example, the abbreviation “$C_3$+” means one or more hydrocarbon molecules of three or more carbon atoms.

As used herein, the term “zone” can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

BRIEF DESCRIPTION OF THE DRAWINGS

The present invention will hereinafter be described in conjunction with the following drawing figures, wherein like numerals denote like elements, and wherein.

Figure 1:
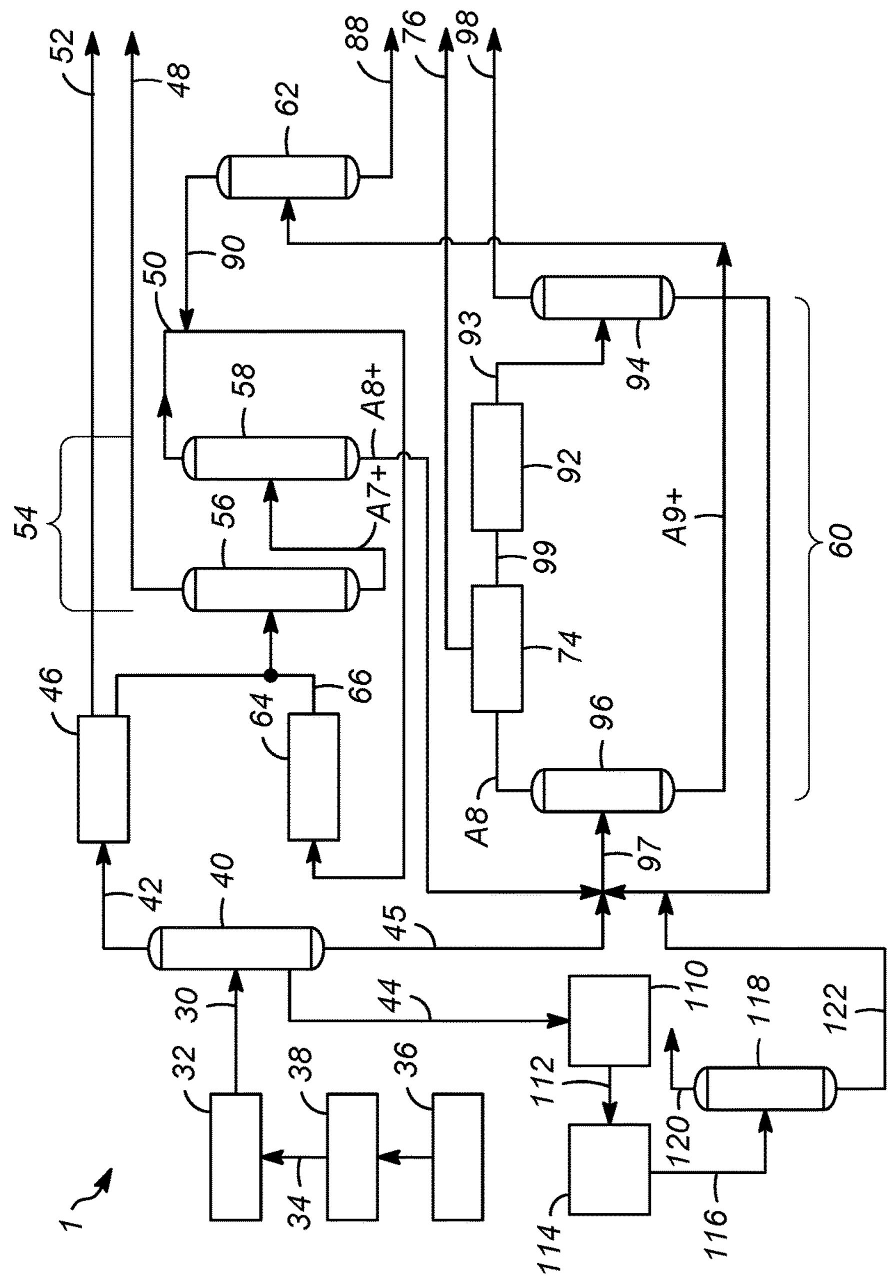
FIG. 1 is a schematic diagram of an aromatics complex for performing a process to increase overall aromatics and xylenes yield, according to an exemplary embodiment of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Various embodiments are directed to processes for increasing overall aromatics and xylenes yield in an aromatics complex by isomerizing higher alkyl group-substituted $C_9$ or $C_9$ and $C_{10}$ ($C_9/C_{10}$) aromatics from an aromatics-rich reformate produced from reforming hydrotreated naphtha and pyrolysis gasoline feedstocks. The aromatics-rich reformate is created via high-severity reforming and typically has higher levels of higher alkyl group-substituted aromatic compounds than are seen at equilibrium at lower reformer temperatures. As used herein, “higher alkyl group-substituted aromatics” refers to aromatic compounds having substituted ethyl, propyl, or butyl groups on the aromatic rings. Ethyl, propyl, and butyl groups are collectively referred to herein as “higher alkyl groups”. For example, the ethyl groups involved in the isomerization reaction are those $C_9$ or $C_9/C_{10}$ aromatics having at least one ethyl substitute, such as diethylbenzene, methyl-ethylbenzene (ethyl-toluene), or dimethyl ethylbenzene. If the higher alkyl group-substituted $C_9$ or $C_9/C_{10}$ aromatics are passed to the transalkylation process unit without prior isomerization to convert a portion of the higher alkyl groups to methyl groups, the higher alkyl groups on the aromatic rings will be dealkylated, forming liquefied petroleum gas (hereinafter “LPG”), i.e., fuel gas, with a higher benzene yield and lower xylenes yield. As noted previously, “dealkylation” refers to the complete or partial removal of the alkyl group(s). Higher ratios of methyl groups to the higher alkyl groups results in higher xylenes yields. Thus, if the higher alkyl groups are not dealkylated in the transalkylation process unit to LPG (fuel gas), but are isomerized to methyl groups forming trimethylbenzene, for example, before transalkylation, the overall aromatics and xylenes yield increases and the hydrogen consumption and fuel gas generation decrease. Isomerization conserves the alkyl groups on the aromatic rings by converting them to methyl groups, preventing their dealkylation during a subsequent transalkylating step.

Referring to FIG. 1, a process for increasing overall aromatics and xylenes yield in an aromatics complex 1 begins by producing an aromatics-rich reformate 30. The aromatics-rich reformate 30 is produced from a reforming process, conducted in a reforming unit 32 in the aromatics complex, by selectively reforming hydrotreated naphtha feed 34, as well known in the art. The naphtha feed 36 is hydrotreated in a hydrotreater 38 to remove sulfur and nitrogen from the naphtha feed producing the hydrotreated naphtha feed 34. The aromatics-rich reformate 30 is sent to a reformate splitter column 40 for separation into a $C_7$− aromatics fraction 42 and a $C_8$-$C_{10}$ aromatics fraction 44, and a $C_{10}$+ aromatics fraction 45. The bottoms fraction would most preferably include the heavier $C_{10}$ aromatics as they are synergistically the products from the subject isomerization step which is limited by equilibrium. These molecules include dimethylethyl benzenes and tetramethylbenzene while the lighter boiling diethylbenzenes and methylpropyl benzenes would preferably be sent to the isomerization reactor in the $C_8$-$C_{10}$ aromatics fraction 44.

As known in the art, the $C_7$− aromatics fraction is sent overhead to be subjected to an extractive distillation process in an extraction process unit 46 of the aromatics complex for extraction of benzene 48 and a toluene-containing stream 50 (Liquid-Liquid extraction can also be applied for certain feedstocks). The extraction process unit extracts benzene and toluene from the reformate splitter column overhead (the $C_7$− aromatics fraction) and rejects a substantially aromatics-free raffinate stream 52, which can be further refined into paraffinic solvents, blended into gasoline, or used as feedstock for an ethylene plant. The aromatics extract is treated to remove trace olefins, and individual high purity benzene and toluene products are recovered in a benzene-toluene fractionation section (hereinafter "BT fractionation section") 54 of the aromatics complex. The BT fractionation section 54 includes a benzene column 56 and a toluene column 58 or alternatively a three product, benzene, toluene, $A_8$+ combined column enabled by an internal dividing wall. Benzene 48 is recovered as a stream from an upper section of the benzene column with $C_7$+ material flowing from the benzene column bottom stream to the toluene column. $A_8$+ aromatics from the bottom stream of the toluene column are sent to a xylenes column 96 at a front end of a xylenes recovery section 60 of the aromatics complex. The claimed subject matter may also apply to an energy conservation flow scheme within an aromatics-processing complex producing xylene isomers as described in U.S. Pat. No. 8,609,922. Further, the claimed subject matter may also apply to apparatuses and methods for processing hydrocarbons during the production of desired isomers of xylene, and more particularly relates to apparatuses and methods for isolating aromatic hydrocarbons having eight carbon atoms ($C_8$), as described in U.S. patent application Ser. No. 14/040,318 and U.S. patent application Ser. No. 14/040,341.

Referring again to FIG. 1, the process continues by passing the $C_8$+ aromatics fraction ($A_8$+) 45 from the reformate splitter into a xylenes column 96. The xylenes column product stream is passed to a para-xylene recovery process unit 74 in the xylenes recovery section 60 of the aromatics complex for recovery of para-xylene 76, as hereinafter described.

Referring still to FIG. 1, process continues by isomerizing the $C_8$-$C_{10}$ aromatics fraction 44 in the isomerization zone 110 to produce a $C_8$-$C_{10}$ isomerization product stream 112. The $C_8$-$C_{10}$ isomerization product stream 112 is passed to a napthene dehydrogenation zone 114 to produce a napthene dehydrogenation zone product stream 116. The napthene dehydrogenation zone product stream 116 is separated in a column 118 into a first napthene dehydrogenation zone product stream 120 comprising $C_7$− aromatics and a second napthene dehydrogenation zone product stream 122 comprising $C_8$+ aromatics. The second napthene dehydrogenation zone product stream 122 comprising $C_8$+ aromatics is then sent to a xylenes recovery section 60.

The isomerization zone comprises using an isomerization catalyst comprising a 12-member ring zeolite or 10-member ring zeolite, a binder, and a platinum-group metal component. However it is also contemplated that other isomerization catalysts may be used. The process of isomerizing comprises a temperature range of about 250° C. to about 450° C. The process of isomerizing comprises a pressure range of about 3 bar to about 15 bar.

The napthene dehydrogenation zone comprises a temperature range of about 250° C. to about 450° C. and a pressure range of about 3 bar to about 15 bar and a pressure range of about 3 bar to about 15 bar.

As well known in the art, separation of a multicomponent feed in a distillation column may not result in a perfect separation of the desired components. For example, a small portion of the desired heavy feed components may be present in the overhead product stream and a small portion of the desired light feed components may be present in the bottom product stream. For example, the lighter boiling overhead stream 120 from the column 118 comprises substantially $C_7$−. The heavier boiling bottom stream 122 from the deheptanizer column 118 comprises substantially all $C_8$+ aromatics having a greater amount of methyl substitutes. As used herein, the term "substantially all" can mean an amount generally of at least 90%, preferably at least 95%, and optimally at least 99%, by weight, of a compound or class of compounds in a stream.

As known in the art, naphthene bridges allow conversion of the $C_8$+ aromatics to different isomers during isomerization, yielding certain fractions of naphthenes in the isomerization product. The isomerization catalyst incorporates an acid function to promote naphthene ring transformation from cyclohexanes to cyclopentanes and back again and a metal function to promote the equilibrium amount of naphthenes to enable substituted ethyl, propyl, and butyl group isomerization to substituted methyl groups, i.e, the ethyl, propyl, and butyl groups on the $C_8$-$C_{10}$ aromatic rings.

The $C_8$+ aromatics fraction of the separated isomerization product becomes part of the hydrocarbons that are passed to the xylenes column 96. The bottoms stream from the xylenes column 96 contains heavies. As used herein, the term "heavies" refers to $C_9$+ aromatics and are sent to the heavy aromatics column 62. The methyl-enriched $C_9$+ aromatics are separated into a $C_{11}$+ aromatics fraction 88 from the bottom stream of the heavy aromatics column and a methyl-enriched $C_9$/$C_{10}$ aromatics fraction 90 from the overhead thereof. The methyl-enriched $C_9$/$C_{10}$ aromatics fraction 90 is sent to a transalkylation process unit 64, after blending with a toluene-containing stream 50 from the overhead of the toluene column 58 in the BT fractionation section 54 of the aromatics complex.

The process continues by transalkylating the methyl-enriched $C_9$/$C_{10}$ aromatics fraction (or the methyl-enriched $C_9$+ aromatics if separation step in heavy aromatics column 62 is not performed) with the toluene-containing stream. Transalkylation effluent 66 is sent to a stripper column (not shown) within the transalkylation process unit to remove light ends, and then recycled to the BT fractionation section 54. As used herein, the term "light ends" refers to $C_6$− compounds, as previously defined. The transalkylation process unit 64 disproportionates toluene into benzene and mixed xylenes and transalkylates the methyl-enriched $C_9$/$C_{10}$ aromatics (or methyl-enriched $C_9$+ aromatics) with the toluene-containing stream into xylenes and benzene, as known in the art. The overhead material (not shown) from the stripper column is separated into gas and liquid products. The overhead gas (not shown) is exported to a fuel gas system, and the overhead liquid is typically recycled back to the extraction unit 46 for recovery of residual benzene. The mixed xylenes are then processed in the xylenes recovery section to produce one or more of the individual xylene isomers, including para-xylene.

In the xylenes recovery section 60 of the aromatics complex, as known to one skilled in the art, the already-separated $C_8$+ aromatics fraction 45 is processed to produce para-xylene 76 in the para-xylene recovery process unit, as previously noted. The separated $C_8$ aromatics fraction is fed into the para-xylene recovery process unit 74. Raffinate 99 from the para-xylene recovery process unit 74 is almost entirely depleted of para-xylene. The raffinate is sent to another isomerization process unit 92, where additional para-xylene is produced by re-establishing an equilibrium distribution of xylene isomers, as known to one skilled in the art. Other aromatics are also produced, in a lesser amount than para-xylene, in the isomerization process unit 92. Effluent 93 from the isomerization process unit 92 is sent to a deheptanizer column 94. The bottom stream from the deheptanizer column comprises $C_7$+ aromatics (primarily mixed xylenes). The bottom stream from the deheptanizer column is recycled back to the xylenes column 96 at a front end of the xylenes recovery section of the aromatics complex, after blending with the $A_8$+ aromatics from the bottom stream of the toluene column, stream 45, and stream 122. The $C_9$/$C_{10}$ aromatics from the bottom stream of the xylenes column is passed to the heavy aromatics column 62. The $C_8$ aromatics from the overhead of the xylenes column is passed to the para-xylene recovery process unit 74 and processed to para-xylene, as previously described. In this way, all the $C_8$ aromatics are continually recycled within the xylenes recovery section of the complex until they exit the aromatics complex as para-xylene or benzene. The overhead stream 98 from the deheptanizer column is split into gas and liquid products. The overhead gas 98 is exported to the fuel gas system and the overhead liquid (not shown) is normally recycled back to the extraction unit 46 for recovery of residual benzene.

Figure 2:
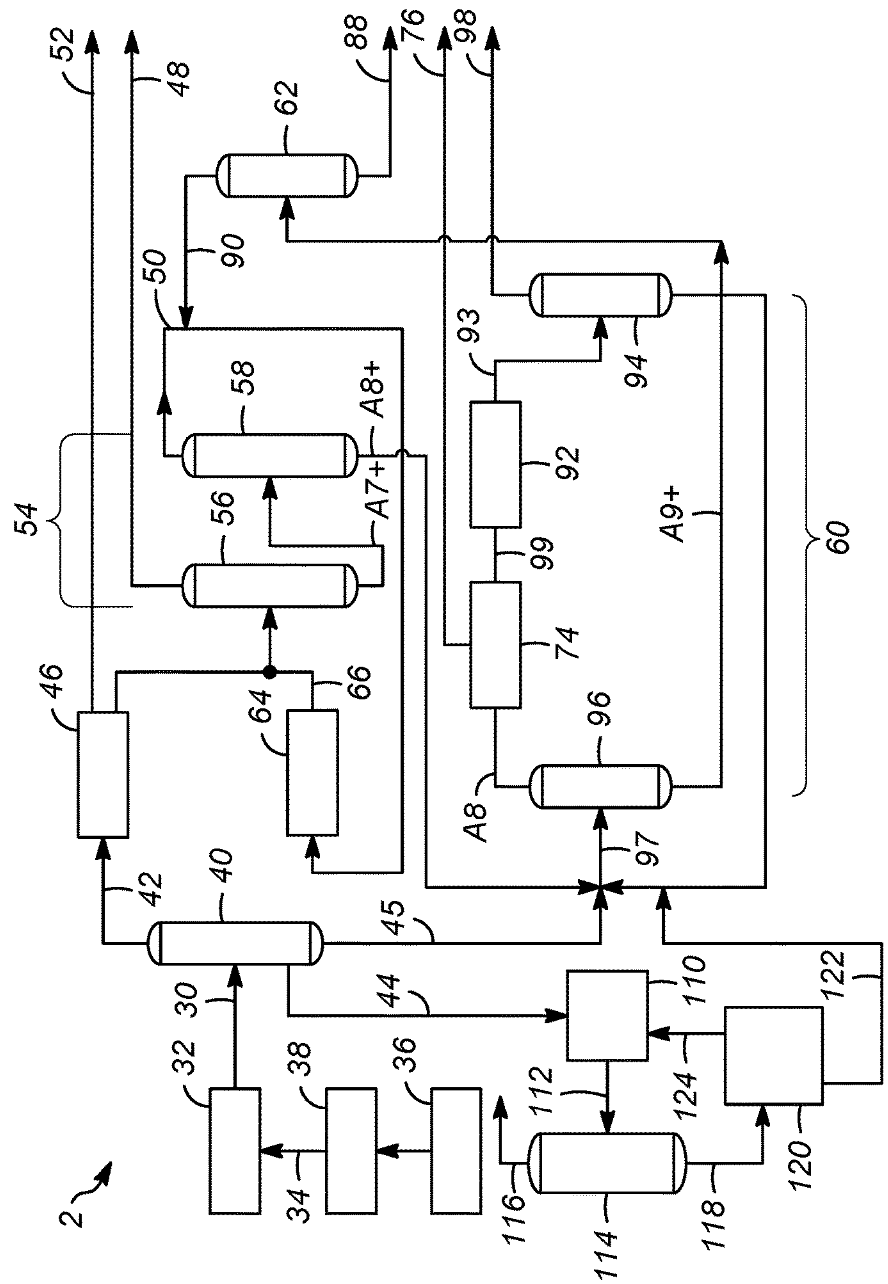
FIG. 2 is another schematic diagram of an aromatics complex for performing the process to increase overall aromatics and xylenes yield, according to another exemplary embodiment of the present invention.

Referring to FIG. 2, another process for increasing overall aromatics and xylenes yield in an aromatics complex 2 begins by producing an aromatics-rich reformate 30. The aromatics-rich reformate 30 is produced from a reforming process, conducted in a reforming unit 32 in the aromatics complex, by selectively reforming hydrotreated naphtha feed 34, as well known in the art. The naphtha feed 36 is hydrotreated in a hydrotreater 38 to remove sulfur and nitrogen from the naphtha feed producing the hydrotreated naphtha feed 34. The aromatics-rich reformate 30 is sent to a reformate splitter column 40 for separation into a $C_7$− aromatics fraction 42 and a $C_8$-$C_{10}$ aromatics fraction 44, and a $C_{10}$+ aromatics fraction 45. The bottoms fraction would most preferably include the heavier $C_{10}$ aromatics as they are synergistically the products from the subject isomerization step which is limited by equilibrium. These molecules include dimethylethyl benzenes and tetramethylbenzene while the lighter boiling diethylbenzenes and methylpropyl benzenes would preferably be sent to the isomerization reactor in the $C_8$-$C_{10}$ aromatics fraction 44.

As known in the art, the $C_7$− aromatics fraction is sent overhead to be subjected to an extractive distillation process in an extraction process unit 46 of the aromatics complex for extraction of benzene 48 and a toluene-containing stream 50 (Liquid-Liquid extraction can also be applied for certain feedstocks). The extraction process unit extracts benzene and toluene from the reformate splitter column overhead (the $C_7$− aromatics fraction) and rejects a substantially aromatics-free raffinate stream 52, which can be further refined into paraffinic solvents, blended into gasoline, or used as feedstock for an ethylene plant. The aromatics extract is treated to remove trace olefins, and individual high purity benzene and toluene products are recovered in a benzene-toluene fractionation section (hereinafter "BT fractionation section") 54 of the aromatics complex. The BT fractionation section 54 includes a benzene column 56 and a toluene column 58 or alternatively a three product benzene, toluene, $A_8$+ combined column enabled by an internal dividing wall. Benzene 48 is recovered as a stream from an upper section of the benzene column with $C_7$+ material flowing from the benzene column bottom stream to the toluene column. $A_8$+ aromatics from the bottom stream of the toluene column are sent to a xylenes column 96 at a front end of a xylenes recovery section 60 of the aromatics complex. The claimed subject matter may also apply to an energy conservation flow scheme within an aromatics-processing complex producing xylene isomers as described in U.S. Pat. No. 8,609,922. Further, the claimed subject matter may also apply to apparatuses and methods for processing hydrocarbons during the production of desired isomers of xylene, and more particularly relates to apparatuses and methods for isolating aromatic hydrocarbons having eight carbon atoms ($C_8$), as described in U.S. patent application Ser. No. 14/040,318 and U.S. patent application Ser. No. 14/040,341.

Referring again to FIG. 2, the process continues by passing the $C_8$+ aromatics fraction ($A_8$+) 45 from the reformate splitter into a xylenes column 96. The xylenes column product stream is passed to a para-xylene recovery process unit 74 in the xylenes recovery section 60 of the aromatics complex for recovery of para-xylene 76, as hereinafter described.

Referring still to FIG. 2, process continues by isomerizing the $C_8$-$C_{10}$ aromatics fraction 44 in the isomerization zone 110 to produce a $C_8$-$C_{10}$ isomerization product stream 112. The $C_8$-$C_{10}$ isomerization product stream 112 is passed to a column 114 to produce an overhead stream 116 comprising $C_7$− aromatics and a bottoms stream 118 comprising $C_8$+ aromatics. The bottoms stream 118 comprising $C_8$+ aromatics is passed to an aromatics recovery zone 120 which produces a first aromatics extraction product stream 124 comprising $C_8$-$C_{10}$ non-aromatics that are sent back to the isomerization zone 110. The second aromatics extraction product stream 122 comprising $C_8$+ aromatics is sent to the xylenes column 96.

The isomerization zone comprises using an isomerization catalyst comprising a 12-member ring zeolite or 10-member ring zeolite, a binder, and a platinum-group metal component. However it is also contemplated that other isomerization catalysts may be used. The process of isomerizing comprises a temperature range of about 250° C. to about 450° C. The process of isomerizing comprises a pressure range of about 3 bar to about 15 bar.

As well known in the art, separation of a multicomponent feed in a distillation column may not result in a perfect separation of the desired components. For example, a small portion of the desired heavy feed components may be present in the overhead product stream and a small portion of the desired light feed components may be present in the bottom product stream. For example, the lighter boiling overhead stream 116 from the column 114 comprises substantially all $C_7$−. The heavier boiling bottom stream 118 from the deheptanizer column 114 comprises substantially all $C_8$+ aromatics and napthenes having a greater amount of methyl substitutes. As used herein, the term "substantially all" can mean an amount generally of at least 90%, preferably at least 95%, and optimally at least 99%, by weight, of a compound or class of compounds in a stream.

As known in the art, naphthene bridges allow conversion of the $C_8$-$C_{10}$ aromatics to different isomers during isomerization, yielding certain fractions of naphthenes in the isomerization product. The isomerization catalyst incorporates an acid function to promote naphthene ring transformation from cyclohexanes to cyclopentanes and back again and a metal function to promote the equilibrium amount of naphthenes to enable substituted ethyl, propyl, and butyl group isomerization to substituted methyl groups, i.e, the ethyl, propyl, and butyl groups on the $C_8$-$C_{10}$ aromatic rings.

The $C_8$+ aromatics fraction of the separated isomerization product becomes part of the hydrocarbons that are passed to the xylenes column 96. The bottoms stream from the xylenes column 96 contains heavies. As used herein, the term "heavies" refers to $C_9$+ aromatics and are sent to the heavy aromatics column 62. The methyl-enriched $C_9$+ aromatics are separated into a $C_{11}$+ aromatics fraction 88 from the bottom stream of the heavy aromatics column and a methyl-enriched $C_9/C_{10}$ aromatics fraction 90 from the overhead thereof. The methyl-enriched $C_9/C_{10}$ aromatics fraction 90 is sent to a transalkylation process unit 64, after blending with a toluene-containing stream 50 from the overhead of the toluene column 58 in the BT fractionation section 54 of the aromatics complex.

The process continues by transalkylating the methyl-enriched $C_9/C_{10}$ aromatics fraction (or the methyl-enriched $C_9$+ aromatics if separation step is not performed) with the toluene-containing stream. Transalkylation effluent 66 is sent to a stripper column (not shown) within the transalkylation process unit to remove light ends, and then recycled to the BT fractionation section 54. As used herein, the term "light ends" refers to $C_6$− compounds, as previously defined. The transalkylation process unit 64 disproportionates toluene into benzene and mixed xylenes and transalkylates the methyl-enriched $C_9/C_{10}$ aromatics (or methyl-enriched $C_9$+ aromatics) with the toluene-containing stream into xylenes and benzene, as known in the art.

The overhead material (not shown) from the stripper column is separated into gas and liquid products. The overhead gas (not shown) is exported to a fuel gas system, and the overhead liquid is typically recycled back to the extraction unit 46 for recovery of residual benzene. The mixed xylenes are then processed in the xylenes recovery section to produce one or more of the individual xylene isomers, including para-xylene.

In the xylenes recovery section 60 of the aromatics complex, as known to one skilled in the art, the already-separated $C_8$+ aromatics fraction 45 is processed to produce para-xylene 76 in the para-xylene recovery process unit, as previously noted. The separated $C_8$ aromatics fraction is fed into the para-xylene recovery process unit 74. Raffinate 99 from the para-xylene recovery process unit 74 is almost entirely depleted of para-xylene. The raffinate is sent to another isomerization process unit 92, where additional para-xylene is produced by re-establishing an equilibrium distribution of xylene isomers, as known to one skilled in the art. Other aromatics are also produced, in a lesser amount than para-xylene, in the isomerization process unit 92. Effluent 93 from the isomerization process unit 92 is sent to a deheptanizer column 94. The bottom stream from the deheptanizer column comprises $C_7$+ aromatics (primarily mixed xylenes). The bottom stream from the deheptanizer column is recycled back to the xylenes column 96 at a front end of the xylenes recovery section of the aromatics complex, after blending with the $A_8$+ aromatics from the bottom stream of the toluene column. The $C_9/C_{10}$ aromatics from the bottom stream of the xylenes column is passed to the heavy aromatics column 62. The $C_8$ aromatics from the overhead of the xylenes column is passed to the para-xylene recovery process unit 74 and processed to para-xylene, as previously described. In this way, all the $C_8$ aromatics are continually recycled within the xylenes recovery section of the complex until they exit the aromatics complex as para-xylene or benzene. The overhead stream 98 from the deheptanizer column is split into gas and liquid products. The overhead gas 98 is exported to the fuel gas system and the overhead liquid (not shown) is normally recycled back to the extraction unit 46 for recovery of residual benzene.

EXAMPLES

The following examples are intended to further illustrate the subject embodiments. These illustrations of different embodiments are not meant to limit the claims to the particular details of these examples.

TABLE

| Includes A8-A10 Isomerization? | No | Yes |
|---|---|---|
| Feeds, kmta | | |
| Reformate | 2000 | 2000 |
| Hydrogen | 12 | 8 |
| Products | | |
| Para-xylene | 1296 | 1409 |
| Light Ends | 153 | 106 |
| Heavy Aromatics | 91 | 79 |
| Raffinate | 174 | 169 |
| Benzene | 297 | 245 |
| Utilities | | |
| Electric, kWh | 14531 | 14339 |
| Medium Pressure Steam, MT/hr | −66 | −57 |
| Boiler Feed Water, MT/hr | 94 | 86 |
| Condensate, MT/hr | −28 | −29 |
| Cooling Water, m3/hr | 402 | 417 |
| Fuel Fired Duty, MMkcal/hr | 290 | 275 |

The Table demonstrates the benefits of incorporating the $A_8$-$A_{10}$ isomerization step. As shown in the Table, by using the same quantity of reformate in the claimed process using the $A_8$-$A_{10}$ isomerization step, the para-xylene yield is increased by 9%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Specific Embodiments

While the following is described in conjunction with specific embodiments, it will be understood that this description is intended to illustrate and not limit the scope of the preceding description and the appended claims.

A first embodiment of the invention is a process for increasing overall xylenes yield in an aromatics complex, the process comprising the steps of separating an aromatics-rich reformate into a first hydrocarbon stream comprising $C_7$− hydrocarbons, a second hydrocarbon stream comprising $C_8$-$C_{10}$ aromatics, and a third hydrocarbon stream comprising $C_{10}$+ aromatics; isomerizing the second hydrocarbon stream comprising $C_8$-$C_{10}$ aromatics to produce a $C_8$-$C_{10}$ isomerization product stream; passing the $C_8$-$C_{10}$ isomerization product stream to a napthene dehydrogenation zone to produce a napthene dehydrogenation zone product stream; separating the napthene dehydrogenation zone product stream into a first napthene dehydrogenation zone product stream comprising $C_7$− hydrocarbons and a second naphthene dehydrogenation zone product stream comprising $C_8$+ aromatics; and passing the second napthene dehydrogenation zone product stream comprising $C_8$+ aromatics to a xylenes recovery section or transalkylation zone. An embodiment of the invention is one, any or all of prior embodiments in this paragraph up through the first embodiment in this paragraph, wherein the step of isomerizing comprises using an isomerization catalyst comprising a 12-member ring zeolite or 10-member ring zeolite, a binder, and a platinum-group metal component. An embodiment of the invention is one, any or all of prior embodiments in this paragraph up through the first embodiment in this paragraph, wherein the step of isomerizing comprises a temperature range of about 250° C. to about 450° C. An embodiment of the invention is one, any or all of prior embodiments in this paragraph up through the first embodiment in this paragraph, wherein the step of isomerizing comprises a pressure range of about 3 bar to about 15 bar. An embodiment of the invention is one, any or all of prior embodiments in this paragraph up through the first embodiment in this paragraph, wherein the napthene dehydrogenation zone comprises a temperature range of about 250° C. to about 550° C. An embodiment of the invention is one, any or all of prior embodiments in this paragraph up through the first embodiment in this paragraph, wherein the napthene dehydrogenation zone a pressure range of about 3 bar to about 15 bar. An embodiment of the invention is one, any or all of prior embodiments in this paragraph up through the first embodiment in this paragraph, wherein separating the second hydrocarbon stream comprising $C_8$-$C_{10}$ aromatics and the third hydrocarbon stream comprising $C_{10}$+ aromatics may be enabled by an internal dividing wall. An embodiment of the invention is one, any or all of prior embodiments in this paragraph up through the first embodiment in this paragraph wherein the second hydrocarbon stream comprising $C_{10}$ aromatic compounds are rich in butyl and methylpropylene benzenes relative to the third hydrocarbon stream.

A second embodiment of the invention is a process for increasing overall xylenes yield in an aromatics complex, the process comprising the steps of separating an aromatics-rich reformate stream into a first hydrocarbon stream comprising $C_7$− hydrocarbons, a second hydrocarbon stream comprising $C_8$-$C_{10}$ aromatics, and a third hydrocarbon stream comprising $C_{10}$+ aromatics; isomerizing the second hydrocarbon stream comprising $C_8$-$C_{10}$ aromatics in a isomerization zone to produce a $C_8$-$C_{10}$ isomerization product stream; separating the $C_8$-$C_{10}$ isomerization product stream into a first isomerization product stream comprising $C_7$− hydrocarbons and a second isomerization product stream comprising $C_8$+ aromatics fraction; passing the second isomerization product stream comprising $C_8$+ aromatics to an aromatics extraction zone to produce a first aromatics extraction zone product stream comprising $C_8$+ non-aromatics and a second aromatics extraction zone product stream comprising $C_8$+ aromatics; passing the first aromatics extraction zone product stream comprising $C_8$+ non-aromatics back to the isomerization zone; and passing the second aromatics extraction zone product stream comprising $C_8$+ aromatics fraction to a xylenes recovery section. An embodiment of the invention is one, any or all of prior embodiments in this paragraph up through the second embodiment in this paragraph, wherein the step of isomerizing comprises using an isomerization catalyst comprising a 12-member ring zeolite or 10-member ring zeolite, a binder, and a platinum-group metal component. An embodiment of the invention is one, any or all of prior embodiments in this paragraph up through the second embodiment in this paragraph, wherein the step of isomerizing comprises a temperature range of about 250° C. to about 450° C. An embodiment of the invention is one, any or all of prior embodiments in this paragraph up through the second embodiment in this paragraph, wherein the step of isomerizing comprises a pressure range of about 3 bar to about 15 bar. An embodiment of the invention is one, any or all of prior embodiments in this paragraph up through the second embodiment in this paragraph, wherein the aromatics extraction zone comprises a temperature range of about 250° C. to about 550° C. An embodiment of the invention is one, any or all of prior embodiments in this paragraph up through the second embodiment in this paragraph, wherein the aromatics extraction zone a pressure range of about 3 bar to about 15 bar. An embodiment of the invention is one, any or all of prior embodiments in this paragraph up through the second embodiment in this paragraph, wherein separating the second hydrocarbon stream comprising $C_8$-$C_{10}$ aromatics and the third hydrocarbon stream comprising $C_{10}$+ aromatics may be enabled by an internal dividing wall. An embodiment of the invention is one, any or all of prior embodiments in this paragraph up through the second embodiment in this paragraph wherein the second hydrocarbon stream comprising Cm aromatic compounds are rich in butyl and methylpropylene benzenes relative to the third hydrocarbon stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for increasing overall xylenes yield in an aromatics complex, the process comprising the steps of:

separating an aromatics-rich reformate into a first hydrocarbon stream comprising $C_7$− hydrocarbons, a second hydrocarbon stream comprising $C_8$-$C_{10}$ aromatics, and a third hydrocarbon stream comprising $C_{10}$+ aromatics;

isomerizing the second hydrocarbon stream comprising $C_8$-$C_{10}$ aromatics to produce a $C_8$-$C_{10}$ isomerization product stream;

passing the $C_8$-$C_{10}$ isomerization product stream to a napthene dehydrogenation zone to produce a napthene dehydrogenation zone product stream;

separating the napthene dehydrogenation zone product stream into a first napthene dehydrogenation zone product stream comprising $C_7$− hydrocarbons and a second naphthene dehydrogenation zone product stream comprising $C_8$+ aromatics; and passing the second napthene dehydrogenation zone product stream comprising $C_8$+ aromatics to a xylenes recovery section or transalkylation zone.

2. The process of claim 1, wherein the step of isomerizing comprises using an isomerization catalyst comprising a 12-member ring zeolite or 10-member ring zeolite, a binder, and a platinum-group metal component.

3. The process of claim 1, wherein the step of isomerizing comprises a temperature range of about 250° C. to about 450° C.

4. The process of claim 1, wherein the step of isomerizing comprises a pressure range of about 3 bar to about 15 bar.

5. The process of claim 1, wherein the napthene dehydrogenation zone comprises a temperature range of about 250° C. to about 550° C.

6. The process of claim 1, wherein the napthene dehydrogenation zone a pressure range of about 3 bar to about 15 bar.

7. The process of claim 1, wherein separating the second hydrocarbon stream comprising $C_8$-$C_{10}$ aromatics and the third hydrocarbon stream comprising $C_{10}$+ aromatics may be enabled by an internal dividing wall.

8. The process of claim 1 wherein the second hydrocarbon stream comprising Cm aromatic compounds are rich in butyl and methylpropylene benzenes relative to the third hydrocarbon stream.

9. A process for increasing overall xylenes yield in an aromatics complex, the process comprising the steps of:

separating an aromatics-rich reformate stream into a first hydrocarbon stream comprising $C_7$− hydrocarbons, a second hydrocarbon stream comprising $C_8$-$C_{10}$ aromatics, and a third hydrocarbon stream comprising $C_{10}$+ aromatics;

isomerizing the second hydrocarbon stream comprising $C_8$-$C_{10}$ aromatics in a isomerization zone to produce a $C_8$-$C_{10}$ isomerization product stream;

separating the $C_8$-$C_{10}$ isomerization product stream into a first isomerization product stream comprising $C_7$− hydrocarbons and a second isomerization product stream comprising $C_8$+ aromatics fraction;

passing the second isomerization product stream comprising $C_8$+ aromatics to an aromatics extraction zone to produce a first aromatics extraction zone product stream comprising $C_8$+ non-aromatics and a second aromatics extraction zone product stream comprising $C_8$+ aromatics;

passing the first aromatics extraction zone product stream comprising $C_8$+ non-aromatics back to the isomerization zone; and passing the second aromatics extraction zone product stream comprising $C_8$+ aromatics fraction to a xylenes recovery section.

10. The process of claim 9, wherein the step of isomerizing comprises using an isomerization catalyst comprising a 12-member ring zeolite or 10-member ring zeolite, a binder, and a platinum-group metal component.

11. The process of claim 9, wherein the step of isomerizing comprises a temperature range of about 250° C. to about 450° C.

12. The process of claim 9, wherein the step of isomerizing comprises a pressure range of about 3 bar to about 15 bar.

13. The process of claim 9, wherein the aromatics extraction zone comprises a temperature range of about 250° C. to about 550° C.

14. The process of claim 9, wherein the aromatics extraction zone a pressure range of about 3 bar to about 15 bar.

15. The process of claim 9, wherein separating the second hydrocarbon stream comprising $C_8$-$C_{10}$ aromatics and the third hydrocarbon stream comprising $C_{10}$+ aromatics may be enabled by an internal dividing wall.

16. The process of claim 9 wherein the second hydrocarbon stream comprising Cm aromatic compounds are rich in butyl and methylpropylene benzenes relative to the third hydrocarbon stream.

* * * * *